United States Patent [19]

Minai et al.

[11] Patent Number: 4,683,323
[45] Date of Patent: * Jul. 28, 1987

[54] METHOD FOR INVERSION OF OPTICALLY ACTIVE 4-HYDROXY-2-CYCLOPENTENONES

[75] Inventors: Masayoshi Minai, Moriyama; Yuji Ueda, Izumi, both of Japan

[73] Assignee: Sumitomo Chemical Company, Limited, Osaka, Japan

[*] Notice: The portion of the term of this patent subsequent to Feb. 18, 2003 has been disclaimed.

[21] Appl. No.: 758,801

[22] Filed: Jul. 25, 1985

[30] Foreign Application Priority Data

Jul. 31, 1984 [JP] Japan .................................. 59-162739
Aug. 3, 1984 [JP] Japan .................................. 59-164018
Sep. 25, 1984 [JP] Japan .................................. 59-199995
Sep. 29, 1984 [JP] Japan .................................. 59-204315

[51] Int. Cl.$^4$ ............................................. C07C 143/68
[52] U.S. Cl. ........................................ 558/52; 568/352
[58] Field of Search .............. 568/379, 347, 341, 352; 260/456 R; 558/52

[56] References Cited

U.S. PATENT DOCUMENTS

| 4,111,994 | 9/1978 | Martel et al. | 568/342 |
|---|---|---|---|
| 4,132,726 | 1/1979 | Kurozumi et al. | 568/379 |
| 4,205,008 | 5/1980 | Martel et al. | 260/456 R |
| 4,367,340 | 1/1983 | Rickards et al. | 568/379 |
| 4,385,186 | 5/1983 | Matsuo et al. | 568/379 |
| 4,552,703 | 11/1985 | Umemura et al. | 568/351 |
| 4,571,436 | 2/1986 | Umemura et al. | 568/354 |

FOREIGN PATENT DOCUMENTS

| 0122779 | 10/1984 | European Pat. Off. | 568/379 |
|---|---|---|---|
| 0127386 | 12/1984 | European Pat. Off. | 568/379 |
| 2355815 | 1/1978 | France | 568/379 |
| 15684077 | 12/1977 | Japan | 260/460 R |
| 15977782 | 10/1982 | Japan | 568/379 |

OTHER PUBLICATIONS

Greene, Protective Groups in Organic Synthesis, pp. ix, 913, 10–13, 107, 299 and 307 (1981).

*Primary Examiner*—James H. Reamer
*Attorney, Agent, or Firm*—Cushman, Darby & Cushman

[57] ABSTRACT

By hydrolyzing a sulfonic acid ester or a nitric acid ester of an optically active 4-hydroxy-2-cyclopentenone, the steric inversion of the hydroxyl group at the 4-position of the cyclopentenone mentioned above is effected.

4-hydroxy-2-cyclopentenone is useful as a raw material of prostaglandins (natural substance is an (R)-substance) having stimulative action to uterine muscle and vasodilator action. For instance, 4(S)-hydroxy-2-cyclopentenone can be configurationally inverted to R-isomer. Accordingly, this method is extremely meaningful in the synthesis of prostaglandins.

30 Claims, No Drawings

METHOD FOR INVERSION OF OPTICALLY ACTIVE 4-HYDROXY-2-CYCLOPENTENONES

The present invention relates to a method for steric inversion of an optically active 4-hydroxy-2-cyclopentenone.

4(R)-hydroxy-2-cyclopentenone which is one of optically active 4-hydroxy-2-cyclopentenones is used as prostaglandins having the same configuration as that of natural material (Japanese Unexamined Patent Publication No. 159777/1982). Accordingly, if 4(S)-hydroxy-2-cyclopentenone having an inverse configuration thereof could be converted to (R)-configuration one, the economical value would be much increased. Also 4(S)-hydroxy-2-cyclopentenone is useful as a new prostaglandins. Accordingly, if 4(R)-hydroxy-2-cyclopentenone could be converted to (S)-configuration one, it would be extremely meaningful in the synthesis of prostaglandins.

Thus, the economical meaning of that the optical configuration of hydroxy group at the 4-position of an optically active 4-hydroxy-2-cyclopentenone can be freely inverted in accordance with each object is extremely important.

Heretofore, as a method for inversion of cyclopentenones, there has been known the following one described in Japanese Unexamined Patent Publication No. 156840/1977:

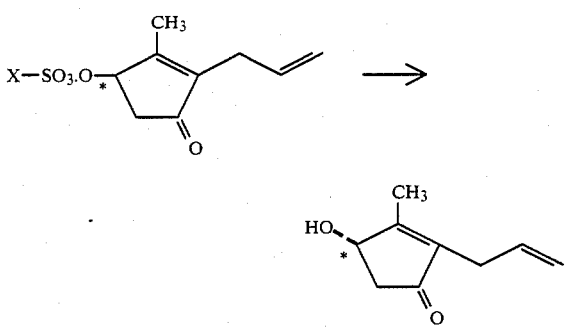

However, there is no disclosure at all on 4-hydroxy-2-cyclopentenone which is the compound aimed at by the present invention. The compound aimed at by the present invention is quite different from the compound described in the Publication in the structure and application. The compound disclosed in the Publication is utilized for a pyrethroidal pesticide called allethrolone, while the compound aimed at by the present invention is utilized as a raw material of prostaglandins which are useful for medicines. As a result, relating to the compound which is the object of the present invention, any point on the reactivity, optical purity or the like thereof has not yet been known.

The present invention provides, relating to such an optically active 4-hydroxy-2-cyclopentenone which is particularly useful as a medicine, a method to conduct the inversion of the optical configuration of the hydroxyl group at the 4-position thereof easily in an industrial scale and with a high optical purity.

That is, the present invention relates to a method for the inversion of an optically active 4-hydroxy-2-cyclopentenone which comprises hydrolyzing a sulfonic acid ester or a nitric acid ester of the raw material optically active 4-hydroxy-2-cyclopentenone having the following formula

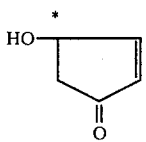

wherein the mark * shows asymmetric carbon atom representing (R)- or (S)-configuration, to obtain an optically active 4-hydroxy-2-cyclopentenone having a configuration as an antipode of the raw material above.

The hydrolysis of the raw material sulfonic acid ester or a nitric acid ester of the optically active 4-hydroxy-2-cyclopentenone is effected by heating the same in the presence of water.

Though this reaction can be carried out without solvent, a solvent may be used.

When the solvent is used, any one may be used without any limitation unless any difficult causes in the reaction; there can be illustrated aprotic polar solvents, ethers, ketones, aliphatic or aromatic hydrocarbons such as, for example, acetone, dimethylformamide, dimethylsulfoxide, acetonitrile, tetrahydrofurane, dioxane, benzene, toluene, methyl isobutyl ketone, dichloromethane, dichloroethane and chlorobenzene or the mixture thereof.

When the solvent is used, though there is no particular limitation on the amount thereof to be used, it is generally 1-20 times the weight of the raw material ester.

Though the necessary amount of water to be used for the hydrolysis is at least an equimolar ratio or more based upon the amount of the raw material ester, it is generally 3 molar ratio or more, preferably in a range of 3.5 molar ratio to 50 molar ratio.

The present hydrolysis is carried out under from neutral to acid conditions. Inorganic or organic acids, for instance, hydrochloric acid, sulfuric acid, phosphoric acid, nitric acid, acetic acid, methanesulfonic acid, p-toluenesulfonic acid are used, when hydrolysis is effected under acid conditions. These acids are usually used in the form of an aqueous solution at the concentration of 0.1–10%. No addition of supplemental acids is necessary during the hydrolysis, since sulfonic acid is by-produced as the hydrolysis proceeds and the solution is kept under acidic. If desired, water-hardly soluble carbonates of alkaline earth metals, such as calcium carbonate, barium carbonate, may be added to the solution. The carbonates fill a role of catching the sulfonic acid by-produced. Alternatively, buffer solutions such as boric acid buffer solution, phosphoric acid buffer solution, acetic acid buffer solution, and phthalic acid-HCl buffer solution may be added in order to have stably the solution kept under neutral to acid.

Preference is that the hydrolysis is carried out under neutral or weak-acid conditions, in order to keep 4-hydroxy-2-cyclopentenone produced at stable condition. Concentration of acids, when used, should be as small as possible. Most preference is the presence of alkaline earth metal carbonates or buffer solution, in order to effect the hydrolysis under neutral conditions.

The reaction temperature in the hydrolysis reaction is 20°–100° C., preferably 40°–90° C. when a sulfonic acid ester is used as the raw material. There is no particular limitation on the reaction time.

On the other hand, when a nitric acid ester is used as the raw material, the reaction temperature is 20°–150° C., preferably 40°–120° C. There is no particular limitation on the reaction time.

Thus, the optical inversion of 4-hydroxy-2-cyclopentenone is effected to obtain an optically active 4-hydroxy-2-cyclopentenone having a configuration as an antipode of the optically active 4-hydroxy-2-cyclopentenone used as the starting raw material in a high yield and a high optical purity.

The isolation of the optically active 4-hydroxy-2-cyclopentenone from the reaction liquid can be easily carried out by usual separation means such as, for instance, extraction, concentration, distillation and chromatography.

SYNTHESIS OF OPTICALLY ACTIVE SULFONIC ACID ESTER OF 4-HYDROXY-2-CYCLOPENTENONE

A sulfonic acid ester of cyclopentenone represented by the general formula:

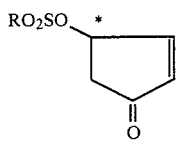

wherein the mark * shows an asymmetric carbon atom and R means a lower alkyl group, trifluoromethyl group or phenyl group which may be substituted is obtained by allowing an optically active 4-hydroxy-2-cyclopentenone represented by the following formula:

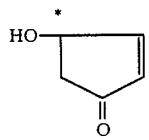

wherein the mark * has the same meaning as the above, representing (R)-configuration or (S)-configuration to react with a sulfonyl halide represented by the general formula:

RSO$_2$X wherein R has the same meaning as the above and X means a halogen atom
in the presence of a base.

The 4-hydroxy-2-cyclopentenone used as the raw material in the present invention is an optically active substance in a form of 4(R)-isomer or 4(R)-isomer.

As the sulfonyl halide which is another raw material, there can be illustrated, for example, alkyl-sulfonyl halides such as methanesulfonyl chloride, ethanesulfonyl chloride, propanesulfonyl chloride and butanesulfonyl chloride or bromides wherein chlorine in the above compounds is substituted with bromine; phenylsulfonyl halides which may be substituted with alkyl, alkoxyl or halogen such as p-toluenesulfonyl chloride, o-toluenesulfonyl chloride, benzenesulfonyl chloride, p-chlorobenzensulfonyl chloride and p-methoxybenzenesulfonyl chloride or bromides wherein chlorine in the above compounds is substituted with bromine; or trifluoromethanesulfonyl chloride.

The reaction of 4-hydroxy-2-cyclopenteneone and sulfonyl halide is usually conducted by condensation in a solvent in the presence of a base.

When a solvent is used in this reaction, there can be illustrated as the solvent those inactive to the reaction such as aliphatic or aromatic hydrocarbons, ether and halogenated hydrocarbons, for example, tetrahydrofuran, dioxane, ethyl ether, acetone, methyl isobutyl ketone, dichloromethane, benzene, toluene, chloroform, chlorobenzene, dimethyl formamide and ethyl acetate or mixture thereof; as to the amount thereof to be used, there is no particular limitation.

The necessary amount of sulfonyl halide to be used in this reaction is 1 equivalent or more per 1 equivalent of 4-hydroxy-2-cyclopentenone; usually it is used in a range of 1–3 equivalents.

As bases, there can be illustrated, for example, organic or inorganic basic materials such as triethylamine, pyridine, picoline, tri-n-butylamine, sodium carbonate, potassium carbonate, sodium hydrogencarbonate and potassium hydrogencarbonate; as to the amount thereof to be used, there is no particular limitation; however, usually it is 1–5 times in equivalent ratio based upon the amount of the raw material 4-hydroxy-2-cyclopentenone.

The reaction temperature is usually in a range of −30°–80° C., preferably −20°–60° C.

There is no particular limitation on the reaction time.

After completion of the reaction, the sulfonic acid ester of cyclopentenone obtained can be isolated from the reaction mixture at a high yield by an operation such as extraction, concentration or chromatography.

However, the product can be used in the form of the reaction mixture as it is in the following hydrolysis and inversion processes without particularly isolating the sulfonic acid ester.

SYNTHESIS OF OPTICALLY ACTIVE NITRIC ACID ESTER OF 4-HYDROXY-2-CYCLOPENTENONE

An optically active nitric acid ester of 4-hydroxy-2-cyclopentenone represented by the following formula:

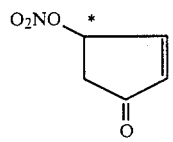

wherein the mark * has the same meaning as the above is obtained by allowing an optically active 4-hydroxy-2-cyclopentenone represented by the formula:

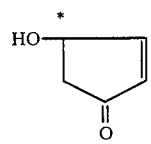

wherein the mark * has the same meaning as the above, representing (R)-configuration or (S)-configuration to react with nitric acid.

The 4-hydroxy-2-cyclopentenone used as the raw material in the present invention is an optically active substance in a form of 4(R)-isomer or 4(S)-isomer.

The reaction of 4-hydroxy-2-cyclopentenone and nitric acid is usually conducted by dehydration condensation in the presence of a solvent.

When a solvent is used in this reaction, there can be illustrated as solvent inactive to the reaction such as aliphatic or aromatic hydrocarbons, ether and halogenated hydrocarbons or the mixture thereof, for example, tetrahydrofuran, dioxane, acetone, ethyl ether, toluene, chloroform and dimethylformamide. The amount thereof to be used is not critical.

The necessary amount of nitric acid to be used in the reaction is 1 equivalent or more per 1 equivalent of 4-hydroxy-2-cyclopentenone, preferably in a range of 1.2-3 equivalents. Of course more amount can be used. As nitric acid, also fuming nitric acid may be used not to speak of normal concentrated nitric acid. Since this reaction is dehydration condensation, as the nitric acid to be used, one having a higher concentration is preferable; usually one having a concentration of 60 wt.% or higher is used.

The use of a dehydrating agent is effective in this reaction. For instance, acetic anhydride or propionic anhydride may be used as a solvent as well as a dehydrating agent. It may be used together with any solvent.

When such a dehydrating agent is used, it is preferable that the amount thereof to be used as 1 equivalent or more based upon the amount of 4-hydroxy-2-cyclopentenone or equimolar ratio or more based upon the water content of the nitric acid to be used. Also it is possible to use nitric acid having a high concentration without using the dehydrating agent.

The reaction temperature is usually in a range of $-40°$–$50°$ C., preferably $-30°$–$35°$ C.

There is no particular limitation on the reaction time.

After completion of the reaction, the nitric acid ester of 4-hydroxy-2-cyclopentenone obtained can be isolated from the reaction mixture by a usual operation such as extraction, concentration or chromatography.

However, the nitric acid ester can be used in the form of concentrated residue as it is in the following hydrolysis and inversion processes without particularly purifying the same.

The present invention will be described with respect to the following Reference Examples and Examples hereinbelow.

SYNTHESIS OF SULFONIC ACID ESTER OF 4-HYDROXY-2-CYCLOPENTENONE

EXAMPLE 1

After 9.8 g of 4(S)-hydroxy-2-cyclopentenone (optical purity: 90%), 50 ml of dichloromethane and 11.9 g of pyridine are charged into a four necked flask equipped with stirrer, thermometer and dropping funnel, 12.6 g of methanesulfonyl chloride is added to the mixture at $-10°$ C. over 2 hours.

After keeping the same temperature for 1 hour, the reaction liquid is washed successively with water, 2% aqueous solution of sodium bicarbonate and water. After drying the organic substance layer over magnesium sulfate, it is concentrated. The concentrated residue is subjected to silica gel column chromatography using a mixture liquid of toluene-ethyl acetate in a ratio of 5:3.

Thus, 16.6 g of methanesulfonic acid ester of 4(S)-hydroxy-2-cyclopentenone is obtained.

$[\alpha]_D^{25} -88.2°$ (C=1, CHCl$_3$).
$n_D^{25}$ 1.4851.

EXAMPLE 2

There is conducted the same reaction as that in Example 1 except that 9.8 g of 4(R)-hydroxy-2-cyclopentenone (optical purity: 96%) is used instead of 4(S)-hydroxy-2-cyclopentenone. After the same aftertreatment and purification as in Example 1, there is obtained 16.4 g of methanesulfonic acid ester of 4(R)-hydroxy-2-cyclopentenone.

$[\alpha]_D^{25} +94.6°$ (C=1, CHCl$_3$).

When the product is left as it is, crystallization takes place.
m.p. 69°–71° C.

EXAMPLE 3

In the same flask as that in Example 1, 4.9 g of 4(R)-hydroxy-2-cyclopentenone (optical purity: 96%), 5.9 g of pyridine and 30 ml of dichloromethane are charged.

To this mixture is added 8.6 g of Propane sulfonyl chloride at 0°–10° C. over 1 hour. Then, the reaction is continued at 0°–10° C. for 2 hours and at 20°–30° C. for 4 hours. After completion of the reaction, the aftertreatment and purification are conducted in accordance with the procedure of Example 1 to obtain 9.5 g of Propane sulfonic acid ester of 4(R)-hydroxy-2-cyclopentenone.

$[\alpha]_D^{25} +81.8°$ (C=1, CHCl$_3$).
$n_D^{25}$ 1.4874.

EXAMPLE 4

There is effected the same reaction as that in Example 3 except that 4(S)-hydroxy-2-cyclopentenone (optical purity: 97%) is used instead of 4(R)-4-hydroxy-2-cyclopentenone. After the same aftertreatment and purification as in Example 3, there is obtained propanesulfonic acid ester of 4(S)-hydroxy-2-cyclopentenone.

$[\alpha]_D^{25} -82°$ (C=1, CHCl$_3$).
$n_D^{25}$ 1.4869.

EXAMPLE 5

In the same flask as that in Example 1, 4.9 g of 4(S)-hydroxy-2-cyclopentenone (optical purity: 97%), 6.9 g of triethylamine and 50 ml of tetrahydrofuran are charged. To this mixture is added 10.9 g of p-toluenesulfonyl chloride at 0°–10° C. over 1 hour. The content is kept at the same temperature for 2 hours and at 25°–30° C. for 5 hours. After completion of the reaction, the reaction liquid is poured into ice water and extracted 2 times with 80 ml of ethyl acetate. The organic layers are collected and washed successively with water, 2% aqueous solution of sodium bicarbonate and water. Then, the aftertreatment and purification are conducted in accordance with the procedure in Example 1 to obtain 11.9 g of p-toluenesulfonic acid ester of 4(S)-hydroxy-2-cyclopentenone.

$[\alpha]_D^{25} -16.0°$ (C=1, CHCl$_3$).
$n_D^{25}$ 1.5648.

EXAMPLE 6

There is effected the same reaction as that in Example 5 except that 4.9 g of 4(R)-hydroxy-2-cyclopentenone. After the same aftertreatment and purification, there is obtained 11.7 g of p-toluenesulfonic acid ester of 4(R)-hydroxy-2-cyclopentenone.

$[\alpha]_D^{25} +14.8°$ (C=1, CHCl$_3$).
$n_D^{25}$ 1.5638.

EXAMPLE 7

In the same flask as that in Example 1, 4.9 g of 4(S)-hydroxy-2-cyclopentenone (optical purity: 90%), 60 ml of methyl isobutyl ketone and 6 g of pyridine are charged. To this mixture is added 10.6 g of benzene-sulfonyl chloride at 5°–10° C. over 1 hour. The content is stirred at the same temperature for 2 hours and at 25°–30° C. for 4 hours. Then, the same aftertreatment and purification are conducted in accordance with the procedure in Example 1 to obtain 11.1 g of benzene-sulfonic acid ester of 4(S)-hydroxy-2-cyclopentenone.

$[\alpha]_D^{25} + 15°$ (C=1, CHCl$_3$).
$n_D^{25}$ 1.5610.

INVERSION REACTION OF SULFONIC ACID ESTER OF 4-HYDROXY-2-CYCLOPENTENONE

EXAMPLE 8

After 8 g of methanesulfonic acid ester of 4(S)-hydroxy-2-cyclopentenone obtained in Example 1, 40 ml of water and 1.2 g of calcium carbonate are mixed, the mixture is heated with stirring at 60° C. for 4 hours.

After completion of the reaction, the reaction liquid is extracted 4 times with 60 ml of methyl isobutyl ketone, and the extracted organic layers are collected and concentrated.

The concentrated residue is purified by silica gel chromatography using a mixture solution of ethyl acetate and toluene in a ratio of 1:1 (by weight) to obtain 4.19 g of 4(R)-hydroxy-2-cyclopentenone.

$[\alpha]_D^{25} + 78.2°$ (C=1, methanol).
Optical purity 84%.

The optical purity is measured by NMR after the product was converted to an ester of (+)-$\alpha$-methoxy-$\alpha$-(trifluoromethyl)-phenylacetic acid.

EXAMPLE 9

After 9.8 g of 4(S)-hydroxy-2-cyclopentenone (optical purity: 97%), 50 ml of dichloromethane and 11.9 g of pyridine are charged into a four necked flask equipped with stirrer, thermometer and dropping funnel, 12.6 g of methanesulfonyl chloride is added to the mixture at −10° C. over 2 hours.

After keeping the same temperature for 1 hour, the reaction liquid is washed successively with water, 2% aqueous solution of sodium bicarbonate and water.

Separately, 80 ml of water and 9.6 g of calcium carbonate are charged in a four necked flask, and the solution is heated up to 60°–70° C. To this solution is added dropwise the dichloromethane solution mentioned above over 1.5 hours. Dichloromethane distilled off is eliminated from the reaction liquid.

After completion of dropwise adding, the mixture is stirred at the same temperature for 4 hours.

After completion of the reaction, the reaction liquid is extracted 4 times with 100 ml of methyl isobutyl ketone. The oleaginous layer extracted is subjected to the aftertreatment and purification in accordance with the procedure in Example 8 to obtain 8.96 g of 4(R)-hydroxy-2-cyclopentenone.

$[\alpha]_D^{25} + 90.4°$ (C=1, methanol).
Optical purity 94.1%.

EXAMPLE 10

Eight grams of methanesulfonic acid ester of 4(R)-hydroxy-2-cyclopentenone obtained in Example 2, 250 ml of water and 25 ml of dioxane are heated with stirring at 80° C. for 3 hours. Then, the aftertreatment and purification are conducted in accordance with the procedure in Example 8 to obtain 4.11 g of 4(S)-hydroxy-2-cyclopentenone.

$[\alpha]_D^{25} - 84.0°$ (C=1, methanol).
Optical purity 87.5%.

EXAMPLE 11

Eight grams of propanesulfonic acid ester of 4(S)-hydroxy-2-cyclopentenone obtained in Example 4, 30 ml of water and 5 g of calcium carbonate are heated with stirring at 60° C. for 3 hours. Then, the aforetreatment and purification are conducted in accordance with the procedure in Example 8 to obtain 3.58 g of 4(R)-hydroxy-2-cyclopentenone.

$[\alpha]_D^{25} + 90.1°$ (C=1, methanol).
Optical purity 93.5%.

EXAMPLE 12

Eleven grams of p-toluenesulfonic acid ester of 4(S)-hydroxy-2-cyclopentenone obtained in Example 5, 30 ml of water, 30 ml of tetrahydrofuran and 10 g of barium carbonate are heated with stirring at 60°–70° C. for 3 hours. After completion of the reaction, insoluble content is eliminated by filtration. Then, the aftertreatment and purification are conducted in accordance with the procedure in Example 8 to obtain 4.12 g of 4(R)-hydroxy-2-cyclopentenone.

$[\alpha]_D^{25} + 88.3°$ C. (C=1, methanol).
Optical purity 92%.

EXAMPLE 13

Eight grams of methanesulfonic acid ester of 4(R)-hydroxy-2-cyclopentenone obtained in Example 2 and 40 ml of water are heated with stirring at 60° C. for 3 hours. After completion of the reaction, the aftertreatment and purification are conducted in accordance with the procedure in Example 8 to obtain 4.21 g of 4(S)-hydroxy-2-cyclopentenone.

$[\alpha]_D^{25} - 75.9°$ (C=1, methanol).
Optical purity 79%.

EXAMPLE 14

After 4.9 g of 4(S)-hydroxy-2-cyclopentenone (optical purity: 90%), 30 ml of dichloromethane and 6 g of pyridine are charged in the same flask as that in Example 8, 10.6 g of benzenesulfonyl chloride is added over 1 hour. Then, the content is stirred at the same temperature for 2 hours and further, at 25°–30° C. for 4 hours.

After completion of the reaction, the product is washed successively with water, 2% aqueous solution of sodium bicarbonate and water.

Separately, 40 ml of water and 4.8 g of calcium carbonate are charged in a four necked flask, and the solution is heated up to 60°–70° C. To this solution is added dropwise the dichloromethane solution mentioned above over 1.5 hours. Dichloromethane distilled off is eliminated from the reaction liquid.

After completion of dropwise adding, the mixture is stirred at the same temperature for 3 hours. Then, the aftertreatment and purification are conducted in accordance with the procedure in Example 9 to obtain 4.5 g of 4(R)-hydroxy-2-cyclopentenone.

$[\alpha]_D^{25} + 82.7°$ (C=1, methanol).
Optical purity 86.6%.

SYNTHESIS OF NITRIC ACID ESTER OF 4-HYDROXY-2-CYCLOPENTENONE

EXAMPLE 15

After 19.6 g of 4(S)-hydroxy-2-cyclopentenone (optical purity: 90%) and 60 g of acetic anhydride are charged in a reaction flask, 18.8 g of fuming nitric acid is added dropwise to the mixture at $-15°$ C.$-5°$ C. over 1 hour. After keeping the same temperature for 1 hour, the reaction mixture is poured into ice water and extracted with 160 ml of ethyl acetate. The organic substance layer is further washed successively with water, 2% aqueous solution of sodium bicarbonate and water. After drying the organic substance layer over magnesium sulfate, it is concentrated.

The concentrated residue is purified by silica gel chromatography with a mixture solution of toluene-ethyl acetate (mixing ratio by weight=5:2) to obtain 25.6 g of nitric acid ester of 4(S)-hydroxy-2-cyclopentenone.

$[\alpha]_D^{25} -71.7°$ (C=1. CHCl$_3$).
$n_D^{25}$ 1.4976.

EXAMPLE 16

In 15 ml of tetrahydrofuran are dissolved 4.9 g of S(-)-4-hydroxy-2-cyclopentenone (optical purity: 97%) and 15 g of acetic anhydride, and 4.4 g of huming nitric acid is added dropwise to this solution at $-10°$ C. over 1 hour.

After keeping the same temperature for 1 hour, the reaction mixture is poured into ice and extracted with 50 ml of ethyl acetate. Then, the aftertreatment and purification are conducted in accordance with the procedure in Example 15 to obtain 6.1 g of nitric acid ester of 4-hydroxy-2-cyclopentenone.

$[\alpha]_D^{25} -76.7°$ (C=1, CHCl$_3$).
$n_D^{25}$ 1.4968.

EXAMPLE 17

In a reaction flask are charged 4.9 g of 4(R)-hydroxy-2-cyclopentenone (optical purity: 95%) and 20 g of acetic anhydride, and the mixture is cooled down to $-15°--10°$ C. At the same temperature, 5 g of fuming nitric acid is added dropwise to the mixture over 30 minutes. After keeping the temperature for 1 hour, the aftertreatment and purification are conducted in accordance with the procedure in Example 15 to obtain 6.36 g of nitric acid ester of 4(R)-hydroxy-2-cyclopentenone.

$[\alpha]_D^{25} +76.0°$ (C=1, CHCl$_3$).
$n_D^{25}$ 1.4988.

INVERSION REACTION OF NITRIC ACID ESTER OF 4-HYDORXY-2-CYCLOPENTENONE

EXAMPLE 18

Six grams of nitric acid ester of 4(S)-hydroxy-2-cyclopentenone obtained in Example 15 and 30 ml of water are heated with stirring at 85°–90° C. for 3 hours.

After completion of the reaction, the reaction mixture is neutralized with 4% aqueous solution of NaOH and extracted 4 times with 40 ml of methyl isobutyl ketone. The methyl isobutyl ketone layers are collected and concentrated. The concentrated residue is purified by silica gel chromatography using a mixture solution of ethyl acetate and toluene in a ratio of 1:1 (by weight) to obtain 3.7 g of 4(R)-hydroxy-2-cyclopentenone.

$[\alpha]_D^{25} +50.2°$ (C=1, methanol).
Optical purity 49%.

The optical purity is measured by NMR after the product was converted to an ester of (+)-$\alpha$-methoxy-$\alpha$-(trifluoromethyl)-phenylacetic acid.

EXAMPLE 19

Four grams of nitric acid ester of 4(S)-hydroxy-2-cyclopentenone obtained in Example 15 and 20 ml of water are heated with stirring at 80°–90° C. for 4 hours.

After completion of the reaction, the aftertreatment and purification are conducted in accordance with the procedure in Example 18 to obtain 2.52 g of 4(R)-hydroxy-2-cyclopentenone.

$[\alpha]_D^{25}$ 52.4° (C=1, methanol).
Optical purity 54.5%.

In the Example mentioned above, quite the same reaction is effected except that the treatment is conducted in such a manner that 20 ml of the aqueous solution shown in Table 1 is used instead of water in the hydrolysis reaction. As a result, the yield, optical rotation and optical purity of the compound obtained are as shown in Table 1.

TABLE 1

| Aqueous solution | Compound aimed at | | |
|---|---|---|---|
| | Yield | $[\alpha]_D^{25}$ (C = 1, methanol) | Optical purity |
| Dioxane-water (1:1) | 2.49 g | +56.2° | 58% |
| 1% aqueous sulfuric acid solution | 2.48 g | +36.6° | 38.4% |

EXAMPLE 20

Six grams of nitric acid ester of 4(R)-hydroxy-2-cyclopentenone obtained in Example 17 and 25 g of 0.5% aqueous solution of hydrochloric acid are heated with stirring at 60°–70° C. for 4 hours. Then, the aftertreatment and purification are conducted in accordance with the procedure in Example 18 to obtain 3.62 g of 4(S)-hydroxy-2-cyclopentenone.

$[\alpha]_D^{25} -36.4°$ (C=1, methanol).
Optical purity 38.2%.

EXAMPLE 21

In a reaction flask are charged 9.8 g of 4(S)-hydroxy-2-cyclopentenone (optical purity: 97%) and 30 g of acetic anhydride, and the mixture is cooled down to $-15°--10°$ C. At the same temperature, 9.4 g of fuming nitric acid is added dropwise to the mixture over 1 hour. After further keeping the same temperature for 1 hour, the reaction mixture is poured into ice water and extracted with 80 ml of dichloromethane. The dichloromethane layer is further washed successively with water, 5% aqueous solution of sodium bicarbonate and water.

To 100 ml of water heated to 85°–90° C. is added the dichloromethane solution mentioned above over 2 hours. Dichloromethane distilled off is eliminated from the reaction liquid. After completion of dropwise adding, the mixture is stirred at the same temperature for 4 hours.

After completion of the reaction, the reaction liquid is extracted 4 times with 100 ml of methyl isobutyl ketone. Then, the aftertreatment and purification are conducted in accordance with the procedure in Example 18 to obtain 8.44 g of 4(R)-hydroxy-2-cyclopentenone.

$[\alpha]_D^{25} +55.5°$ (C=1, methanol).
Optical purity 59%.

EXAMPLE 22

With 30 ml of water and 3 g of calcium carbonate, 6 g of nitric acid ester of 4(S)-hydroxy-2-cyclopentenone obtained in Example 15 is heated with stirring at 70°–90° C. for 4 hours.

After completion of the reaction, the reaction mixture is extracted with methyl isobutyl ketone. Then, the aftertreatment and purification are conducted in accordance with the procedure in Example 18 to obtain 2.2 g of 4(R)-hydroxy-2-cyclopentenone.

$[\alpha]_D^{25} +61.6°$ (C=1, methanol).
Optical purity 65%.

EXAMPLE 23

A mixture of 4 g of methanesulfonic acid ester of 4(S)-hydroxy-2-cyclopentenone obtained in Example 1 and 30 ml of 3M phosphoric acid buffer (pH 7) is stirred at 60° C. for 4 hours. After the reaction is over, the reaction mixture is extracted four times with 40 ml of methyl isobutyl ketone. The organic layers are collected and concentrated. The concentrated residue is purified by column chromatography with a mixture solution of ethyl acetate and toluene in a ratio of 1:1 (by weight) to obtain 2.1 g of 4(R)-hydroxy-2-cyclopentenone.

$[\alpha]_D^{25} +82.9°$ (C=1, methanol).
Optical purity 86.3%.

We claim:

1. A method for inversion of an optically active 4-hydroxy-2-cyclopentenone which comprises hydrolyzing under neutral or acid conditions a sulfonic acid ester of the raw material optically active 4-hydroxy-2-cyclopentenone having the following formula

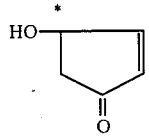

wherein the mark * shows asymmetric carbon atom representing (R)- or (S)-configuration,
to obtain an optically active 4-hydroxy-2-cyclopentenone having a configuration as an antipode of the raw material above.

2. The method according to claim 1, wherein the inversion is effected without solvent or in the presence of a solvent.

3. The method according to claim 2, wherein the solvent is aprotic polar solvents, ethers, ketones, aliphatic or aromatic hydrocarbons such as acetone, dimethylformamide, dimethylsulfoxide, tetrahydrofuran, dioxane, benzene, toluene, methyl isobutyl ketone, dichloromethane, dichloroethane and chlorobenzene or the mixture thereof.

4. The method according to claim 3, wherein the amount of solvent to be used is 1–20 times the weight of the raw material ester.

5. The method according to claim 1, wherein the amount of water to be used for the hydrolysis reaction is at least an equimolar ratio or more based upon the amount of the raw material ester.

6. The method according to claim 5, wherein the amount of water to be used for the hydrolysis reaction is 3 molar ratio or more based upon the amount of the raw material ester.

7. The method according to claim 6, wherein the amount of water to be used for the hydrolysis reaction is 3.5 molar ratio–50 molar ratio based upon the amount of the raw material ester.

8. The method according to claim 1, wherein the acid to be used for the hydrolysis reaction is hydrochloric acid, sulfuric acid, phosphoric acid, nitric acid, acetic acid, methanesulfonic acid and p-toluenesulfonic acid.

9. The method according to claim 8, wherein the concentration of the acid is 0.1–10 wt.%.

10. The method according to claim 1, wherein the hydrolysis reaction is carried out in the presence of alkaline earth metal carbonate.

11. The method according to claim 10, wherein alkaline earth metal carbonate is barium carbonate or calcium carbonate.

12. The method according to claim 1, wherein the hydrolysis is conducted in buffer solution.

13. The method according to claim 12, wherein the buffer solution is a boric acid solution, phosphoric acid solution, acetic acid solution, or phthalic acid-HCl solution.

14. The method according to claim 1, wherein the hydrolysis reaction is conducted in only water.

15. The method according to claim 1, wherein the temperature of the hydrolysis reaction is 20°–100° C. when a sulfonic acid ester is used as the raw material.

16. The method according to claim 15, wherein the temperature of the hydrolysis reaction is 40°–90° C.

17. The method according to claim 1, wherein the temperature of the hydrolysis reaction is 20°–150° C. when a nitric acid ester is used as the raw material.

18. The method according to claim 17, wherein the temperature of the hydrolysis reaction is 40°–120° C.

19. The method according to claim 1, wherein the raw material sulfonic acid ester of 4-hydroxy-2-cyclopentenone represented by the formula:

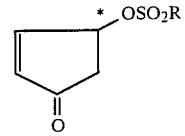

wherein the mark * shows asymmetric carbon atom representing (R)- or (S)-configuration and R means a lower alkyl group, trifluoromethyl group or phenyl group which may be substituted, is obtained by allowing 4-hydroxy-2-cyclopentenone to react with a sulfonyl halide represented by the formula:

wherein R has the same meaning as the above and X means a halogen atom, in the presence of a base.

20. The method according to claim 19, wherein the sulfonyl halide is alkylsulfonyl halides such as methanesulfonyl chloride, ethanesulfonyl chloride, propanesulfonyl chloride and butanesulfonyl chloride or bromides wherein chlorine in the above compounds is substituted with bromine; phenylsulfonyl halides which may be substituted such as p-toluenesulfonyl chloride, O-toluenesulfonyl chloride benzensulfonyl chloride, p-chlorobenzenesulfonyl chloride and p-methoxybenzenesulfonyl chloride or bromides wherein chlorine in the above compounds is substituted with bromine; or trifluoromethanesulfonyl chloride.

21. The method according to claim 19, wherein the amount of sulfonyl halide to be used is 1 equivalent or more per 1 equivalent of 4-hydroxy-2-cyclopentenone.

22. The method according to claim 21, wherein the amount of sulfonyl halide to be used is 1 to 3 equivalents per 1 equivalent of 4-hydroxy-2-cyclopentenone.

23. The method according to claim 19, wherein the base is an organic or inorganic base such as triethylamine, pyridine, picoline, tri-n-butylamine, sodium carbonate, potassium carbonate, sodium hydrogencarbonate or potassium hydrogencarbonate.

24. The method according to claim 19, wherein the amount of the base to be used is 1 to 5 times in equivalent ratio based upon the amount of the raw material 4-hydroxy-2-cyclopentenone.

25. The method according to claim 19, wherein the reaction temperature is $-30°$ C. to $80°$ C.

26. The method according to claim 19, wherein the reaction temperature is $-20°$ C. to $60°$ C.

27. The method according to claim 19, wherein the sulfonic acid esterification reaction of the raw material 4-hydroxy-2-cyclopentenone is conducted in the presence of a solvent inactive to the reaction such as an aliphatic or aromatic hydrocarbon, ether or halogenated hydrocarbon, for example, tetrahydrofuran, dioxane, acetone, ethyl ether, toluene, chloroform or dimethylformamide, dichloromethane or the mixture thereof.

28. The method according to claim 19, wherein the raw material 4-hydroxy-2-cyclopentenone is 4(R)-isomer or 4(S)-isomer.

29.

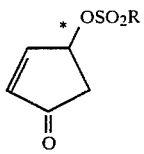

where R is a lower alkyl group, a trifluoromethyl group, a phenyl group, or a substituted phenyl group, which compound is a sulfonic acid ester of the optically active 4-hydroxy-2-cyclopentenone.

30. The method of claim 1 wherein there is employed an acid in a concentration of 0.1–10 wt.%.

* * * * *